(12) United States Patent
Akashe et al.

(10) Patent No.: US 8,765,030 B2
(45) Date of Patent: Jul. 1, 2014

(54) PREPARATION OF AN ENTERIC RELEASE SYSTEM

(75) Inventors: Ahmad Akashe, Mundelein, IL (US); Anilkumar Ganapati Gaonkar, Buffalo Grove, IL (US); Les Lawrence, Rolling Meadows, IL (US); Amado R. Lopez, Chicago, IL (US); Ronald L. Meibach, Deerfield, IL (US); Dana Sebesta, Plano, IL (US); Yan Wang, Glenview, IL (US); James D. White, Hanover Park, IL (US)

(73) Assignee: Intercontinental Great Brands LLC, East Hanover, NJ (US)

( * ) Notice: Subject to any disclaimer, the term of this patent is extended or adjusted under 35 U.S.C. 154(b) by 0 days.

(21) Appl. No.: 13/475,645

(22) Filed: May 18, 2012

(65) Prior Publication Data

US 2012/0273982 A1 Nov. 1, 2012

Related U.S. Application Data

(63) Continuation of application No. 12/479,454, filed on Jun. 5, 2009, now abandoned.

(51) Int. Cl.
*A61K 9/127* (2006.01)

(52) U.S. Cl.
USPC .......................................................... 264/4.3

(58) Field of Classification Search
None
See application file for complete search history.

(56) References Cited

U.S. PATENT DOCUMENTS

| | | | |
|---|---|---|---|
| 2,464,204 A | 3/1949 | Baker | |
| 2,727,833 A | 12/1955 | Chu Yen et al. | |
| 3,010,953 A | 11/1961 | Unger et al. | |
| 3,041,289 A | 6/1962 | Katchen et al. | |
| 3,116,206 A * | 12/1963 | Brynko et al. | 424/491 |
| 3,869,406 A | 3/1975 | Matsukawa et al. | |
| 3,956,172 A | 5/1976 | Saeki et al. | |
| 4,518,458 A | 5/1985 | Greenfield et al. | |
| 4,601,863 A | 7/1986 | Shioi et al. | |
| 4,702,798 A | 10/1987 | Bonanno | |
| 4,778,781 A | 10/1988 | Washizu et al. | |
| 4,895,725 A | 1/1990 | Kantor et al. | |
| 4,936,916 A | 6/1990 | Shinmitsu et al. | |
| 5,051,304 A | 9/1991 | David et al. | |
| 5,051,305 A | 9/1991 | Whitaker, Sr. | |
| 5,146,758 A | 9/1992 | Herman | |
| 5,160,742 A | 11/1992 | Mazer et al. | |
| 5,164,210 A | 11/1992 | Campbell et al. | |
| 5,480,656 A | 1/1996 | Okada et al. | |
| 5,601,760 A | 2/1997 | Rosenberg | |
| 5,679,377 A | 10/1997 | Bernstein et al. | |
| 5,686,092 A | 11/1997 | Lewis | |
| 5,879,541 A | 3/1999 | Parkinson | |
| 5,958,388 A | 9/1999 | Franks | |
| 6,143,170 A | 11/2000 | Briggs et al. | |
| 6,608,017 B1 * | 8/2003 | Dihora et al. | 510/349 |
| 6,653,288 B1 | 11/2003 | Beuvry et al. | |
| 6,770,285 B2 | 8/2004 | Keenan et al. | |
| 6,921,539 B2 | 7/2005 | Ninkov | |
| 6,923,988 B2 | 8/2005 | Patel et al. | |
| 6,929,810 B2 | 8/2005 | Purohit et al. | |
| 6,929,814 B2 | 8/2005 | Bouwmeesters et al. | |
| 7,067,153 B2 | 6/2006 | Grisoni | |
| 7,182,959 B2 | 2/2007 | Martani | |
| 7,192,542 B2 | 3/2007 | Ugazio | |
| 7,250,185 B2 | 7/2007 | Dowdle et al. | |
| 7,279,495 B2 | 10/2007 | Ducray et al. | |
| 7,338,928 B2 | 3/2008 | Lau et al. | |
| 7,427,407 B2 | 9/2008 | Kume et al. | |
| 7,541,155 B2 | 6/2009 | Enan | |
| 7,585,538 B2 | 9/2009 | Mangos et al. | |
| 7,622,269 B2 | 11/2009 | Enan | |
| 2002/0055537 A1 | 5/2002 | Gerlach et al. | |
| 2002/0173522 A1 | 11/2002 | Redmon et al. | |
| 2002/0193452 A1 | 12/2002 | Brocker et al. | |
| 2003/0082272 A1 | 5/2003 | Bouwmeesters et al. | |
| 2003/0175403 A1 | 9/2003 | Gurin | |
| 2003/0180369 A1 | 9/2003 | Grisoni | |
| 2003/0203848 A1 | 10/2003 | Vertesy et al. | |
| 2003/0225003 A1 | 12/2003 | Ninkov | |
| 2003/0228369 A1 | 12/2003 | Kuhrts | |
| 2004/0109894 A1 | 6/2004 | Shefer et al. | |
| 2004/0191366 A1 | 9/2004 | Mangos et al. | |
| 2004/0195711 A1 | 10/2004 | Hayashi et al. | |
| 2004/0266888 A1 | 12/2004 | Ninkov | |

(Continued)

FOREIGN PATENT DOCUMENTS

| EP | 0 579 435 A1 | 1/1994 |
|---|---|---|
| EP | 0 827 997 A1 | 3/1998 |

(Continued)

OTHER PUBLICATIONS

C. L. Kruger and S.W. Mann, Safety evaluation of functional ingredients, Food and Chemical Toxicology, vol. 41, No. 6, Jan. 1, 2003, pp. 793-805, XP009144244, Pergamon, Great Britain.

Claudia S. Leopold and David R. Friend, "In vitro study for the assessment of poly(L-aspartic acid) as a drug carrier for colon-specific drug delivery," International Journal of Pharmaceutics, vol. 126, 1995, pp. 139-145.

European Patent Office Extended European Search Report for European Application No. 10251026.0 dated Aug. 30, 2010 (7 pages).

European Patent Office Extended European Search Report for European Application 10251044.3 dated Feb. 21, 2011 (6 pages).

(Continued)

*Primary Examiner* — Suzanne Ziska
(74) *Attorney, Agent, or Firm* — Fitch, Even, Tabin & Flannery LLP

(57) ABSTRACT

Hydrophobic liquids are microencapsulated by an enteric matrix in an environment substantially free of organic solvents, the process including forming an emulsion of the enteric material and hydrophobic liquid in water, the emulsion titrated with an acid to form a particulate precipitate of the microencapsulated hydrophobic liquid in an enteric matrix.

31 Claims, 4 Drawing Sheets

(56) References Cited

U.S. PATENT DOCUMENTS

| | | | |
|---|---|---|---|
| 2005/0014827 A1* | 1/2005 | Schur | 514/553 |
| 2005/0054682 A1 | 3/2005 | Phillips | |
| 2005/0079138 A1 | 4/2005 | Chickering, III et al. | |
| 2005/0100640 A1 | 5/2005 | Pearce | |
| 2005/0123603 A1 | 6/2005 | Dalland et al. | |
| 2005/0181059 A1 | 8/2005 | Jacob et al. | |
| 2005/0200035 A1 | 9/2005 | Dobbs | |
| 2005/0287276 A1 | 12/2005 | Lavoie et al. | |
| 2006/0134282 A1 | 6/2006 | Mellema | |
| 2006/0147503 A1 | 7/2006 | Floyd | |
| 2006/0280795 A1 | 12/2006 | Penhasi et al. | |
| 2007/0072944 A1 | 3/2007 | Gauvry et al. | |
| 2007/0134332 A1 | 6/2007 | Turnell et al. | |
| 2007/0141147 A1 | 6/2007 | Heil et al. | |
| 2007/0145326 A1 | 6/2007 | Joseph et al. | |
| 2007/0148198 A1 | 6/2007 | Joseph et al. | |
| 2007/0190080 A1* | 8/2007 | Friedman | 424/400 |
| 2007/0218125 A1 | 9/2007 | Head et al. | |
| 2008/0020078 A1 | 1/2008 | Enan | |
| 2008/0029625 A1 | 2/2008 | Talton | |
| 2008/0038362 A1 | 2/2008 | Park et al. | |
| 2008/0125461 A1 | 5/2008 | Barberich | |
| 2008/0145462 A1* | 6/2008 | Enan | 424/757 |
| 2008/0193531 A1 | 8/2008 | Hermelin et al. | |
| 2008/0207766 A1 | 8/2008 | Devane | |
| 2008/0226623 A1 | 9/2008 | Margolin et al. | |
| 2008/0226649 A1 | 9/2008 | Schetter et al. | |
| 2008/0226684 A1 | 9/2008 | Peppas | |
| 2008/0255498 A1 | 10/2008 | Houle | |
| 2008/0260819 A1 | 10/2008 | Fleming et al. | |
| 2008/0299087 A1 | 12/2008 | Tseng et al. | |
| 2009/0186096 A1 | 7/2009 | Kritzman et al. | |
| 2009/0215892 A1 | 8/2009 | Nahab et al. | |
| 2010/0310726 A1 | 12/2010 | Akashe et al. | |
| 2011/0008471 A1 | 1/2011 | Enan | |
| 2011/0020520 A1 | 1/2011 | Van Lengerich et al. | |
| 2011/0124502 A1 | 5/2011 | Enan | |
| 2012/0251641 A1 | 10/2012 | Enan et al. | |

FOREIGN PATENT DOCUMENTS

| | | | |
|---|---|---|---|
| EP | 1 396 551 A1 | 3/2004 | |
| EP | 1 721 605 A1 | 11/2006 | |
| JP | 52-152876 A | 12/1977 | |
| JP | S63-197540 A | 8/1988 | |
| JP | H02-103289 A | 4/1990 | |
| JP | 04-330934 A | 11/1992 | |
| JP | 05-017338 A | 1/1993 | |
| JP | 08-026930 A | 1/1996 | |
| JP | 10-273650 A | 10/1998 | |
| JP | 2003-012526 A | 1/2003 | |
| JP | 2004-018443 A | 1/2004 | |
| JP | 2007-177129 A | 7/2007 | |
| JP | 2008-013529 A | 1/2008 | |
| RU | 2 098 121 C1 | 12/1997 | |
| RU | 2 332 257 C2 | 3/2006 | |
| SU | 447163 A1 | 10/1974 | |
| WO | 82/02496 A1 | 8/1982 | |
| WO | 84/03201 A1 | 8/1984 | |
| WO | 93/19622 A2 | 10/1993 | |
| WO | 00/36924 A1 | 6/2000 | |
| WO | 02/38181 A2 | 5/2002 | |
| WO | 03/097015 A1 | 11/2003 | |
| WO | 2005/082320 A1 | 9/2005 | |
| WO | 2006/093838 A1 | 9/2006 | |
| WO | 2007/044437 A2 | 4/2007 | |
| WO | 2007/094000 A2 | 8/2007 | |
| WO | 2008/003996 A1 | 1/2008 | |
| WO | 2009/117623 A2 | 9/2009 | |

OTHER PUBLICATIONS

Intellectual Property Office of New Zealand Examination Report dated Jun. 1, 2010 for New Zealand Application 585723, 3 pages.

Intellectual Property Office of New Zealand Examination Report dated Jun. 2, 2010 for New Zealand Application 585724, 3 pages.

Intellectual Property Office of New Zealand Examination Report dated Jun. 2, 2010 for New Zealand Application 585725, 3 pages.

L. R. Salgueiro et al., "Chemical Composition and Antifungal Activity of the Essential Oil of *Origanum virens* on *Candida* Species," Planta Med, vol. 69, 2003, pp. 871-874.

M. A. Del Nobile et al., Antimicrobial efficacy and release kinetics of thymol from zein films, Journal of Food Engineering, vol. 89, No. 1, Nov. 1, 2008, pp. 57-63, XP022704837, Barking, Essex, Great Britain.

Nicholas Parris et al., Encapsulation of Essential Oils in Zein Nanospherical Particles, Journal of Agricultural and Food Chemistry, vol. 53, Jun. 15, 2005, pp. 4788-4792, XP-002599360, American Chemical Society, United States of America.

Parag Kolhe et al., "Preparation, cellular transport, and activity of polyamidoamine-based dendritic nanodevices with a high drug payload," Biomaterials, vol. 27, 2006, pp. 660-669.

Pavan Muttil et al., "Inhalable microparticles containing large payload of ani-tuberculosis drugs," European Journal of Pharmaceutical Sciences, vol. 32, 2007, pp. 140-150.

Sunil A. Agnihotri et al., "Recent advances on chitosan-based micro- and nanoparticles in drug delivery," Journal of Controlled Release, vol. 100, 2004, pp. 5-28.

PCT International Searching Authority International Search Report and Written Opinion for International Application No. PCT/US2011/065828 dated May 23, 2012, 11 pages.

Max S. Dunn and Howard B. Lewis, "The Action of Nitrous Acid on Casein," Journal of Biological Chemistry, vol. 49, 1921, pp. 327-341.

L. K. Ramachandran and W. B. McConnell, "The Action of Sulphuric Acid on Gliadin: With Special Reference to the N-Peptidyl→O-Peptidyl Bond Rearrangement," Canadian Journal of Chemistry, vol. 33, 1955, pp. 1638-1648.

R. M. Allison et al., "Notes on a deamination method proposed for determining 'chemically available lysine' of proteins," British Journal of Nutrition, vol. 29, 1973, pp. 51-55.

J. W. Paulis, "Disulfide Structures of Zein Proteins from Corn Endosperm," Cereal Chemistry, vol. 58, No. 6, 1981, pp. 542-546.

Microencapsulation of Food Ingredients, Edited by Per Vilstrup, Leatherhead Food RA Publishing, 2001, pp. 5-6.

LinShu Liu et al., "Pectin/Zein Beads for Potential Colon-Specific Drug Delivery: Synthesis and in Vitro Evaluation," 2006a, vol. 13, pp. 417-423.

Japan Patent Office Official Notice of Rejection dated Mar. 11, 2014 for Japanese Patent Application No. 2010-126987 and informal English Translation, 7 pages.

Ain Raal et al., "Content and composition of the essential oil of *Thymus serpyllum* L. growing wild in Estonia," Medicina (Kaunas), 2004,40(8), 795-800.

SIDS Initial Assessment Report for SIAM 14 dated Mar. 2002, Linalyl Acetate CAS No. 115-95-7, http://www.chem.unep.ch/irptc/sids/OECDSIDS/115957, 57 pages.

Wikipedia entry for Lavender oil, 2013, http://en.wikipedia.org/wiki/Lavender_oil, 5 pages.

\* cited by examiner

Table-1 Data analysis for samples from examples 2, 4 and 5

|  | α-Pinene (wt %) | p-Cymene (wt %) | Linalool (wt %) | Thymol (wt %) | TAGs (wt %) | Sum without TAGs (wt %) | Sum med (wt %) |
|---|---|---|---|---|---|---|---|
| Example 2 | 0.59 | 5.6 | 2.5 | 14.1 | <0.01 | 22.8 | 22.8 |
| Example 4 | 2.1 | 8.1 | 2.5 | 8.0 | 7.8 | 20.7 | 28.4 |
| Example 5 | 0.75 | 2.8 | 1.0 | 8.2 | 7.4 | 12.8 | 20.2 |

PREPARATION OF AN ENTERIC RELEASE SYSTEM

CROSS-REFERENCE TO RELATED APPLICATION

This application is a continuation of prior application Ser. No. 12/479,454, filed Jun. 5, 2009, which is hereby incorporated herein by reference in its entirety.

FIELD OF THE INVENTION

The present application relates to methods for microencapsulating a hydrophobic liquid with an enteric matrix without use of organic solvents. More particularly, the hydrophobic liquid is microencapsulated in an aqueous environment.

BACKGROUND

Enteric delivery of active materials in food delivery applications has been limited. Enteric delivery systems are commonly utilized when the active materials or medicants are known to be sensitive to low pH or have undesirable flavor and/or taste characteristics which cannot be effectively masked by other methods. Generally, enteric delivery is accomplished using tablets and gel capsules. However, those particular delivery methods are not well suited for food applications. In particular, neither tablets nor capsules are sized to be integrated into most existing food products.

An alternative process for enteric delivery is microencapsulation. Microencapsulation is generally performed using specialized equipment or in an environment including organic solvents. These methods require additional capital expenditures and the use of additional materials, such as the organic solvents, which may or may not be usable in subsequent microencapsulation cycles. As a result, the process of microencapsulation requires investments in both equipment and organic solvent procurement and disposal.

SUMMARY

A method is provided for microencapsulating an active ingredient within an enteric matrix in an aqueous environment and without the use of organic solvents. Microencapsulating in an aqueous environment allows for easier working conditions and reduced organic waste.

A method is provided for microencapsulating an active ingredient with an enteric matrix. The method includes agitating or mixing a combination of water, an enteric matrix material, and an emulsifier, at a pH that maintains complete dissolution of the enteric polymers being utilized, the combination being substantially free of organic solvents. A hydrophobic liquid is then added to the combination. The hydrophobic liquid and combination is then agitated to create a coarse emulsion, followed by homogenization to create a fine and stable emulsion.

The emulsion can then be acid titrated under controlled mixing conditions in an amount and a rate effective to form a particulate precipitate. Further, the particulate precipitate can be filtered, washed and dried to form a powder. In one embodiment a surface oil remover can be added to the precipitate after filtering to remove surface oil from the microencapsulated material.

Further, a composition is provided which includes a hydrophobic liquid and a cross-linked enteric matrix.

DETAILED DESCRIPTION

Figure 1:
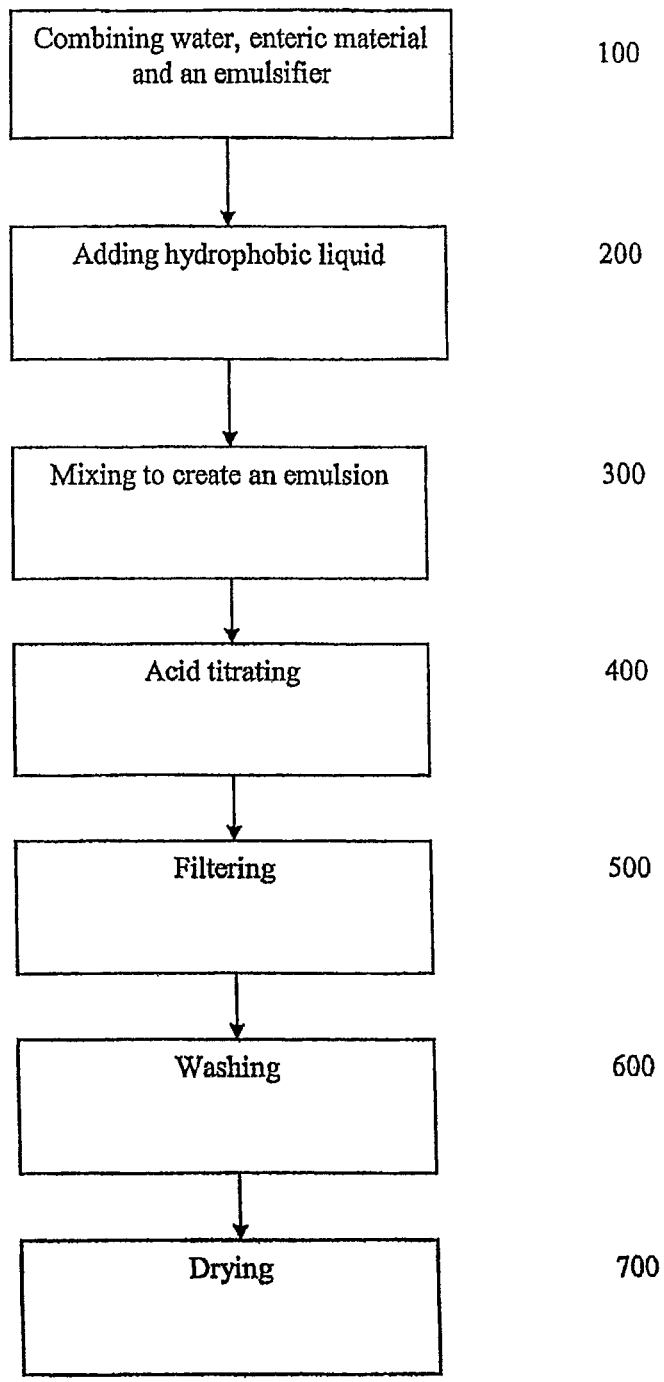
FIG. 1 illustrates a method for microencapsulating a hydrophobic liquid.

A method for microencapsulating a hydrophobic liquid is generally described in FIG. 1.

As shown in FIG. 1, water, an enteric matrix material and an emulsifier are subjected to agitation until the enteric matrix material and emulsifier are fully dispersed in the water 100. Generally, the emulsifier and enteric matrix material can be added to the water together or separately, with either being added first. The pH of the dispersion is generally between about 7.2 and 9.0. In some embodiments, a base, such as sodium, ammonium or potassium hydroxide, can be added to the dispersion to raise the pH to a range from about 7.1 to about 12.0 to guarantee and maintain complete dissolution of the enteric polymers without the use of organic solvents.

As used herein, "agitation" or "agitated" refers to the use of a top entering mixer with impeller or a rotor/stator mixing device operating at a speed of less than 10,000 RPM.

As used herein, "substantially free of organic solvent" refers to an amount of added organic solvent, such as isopropanol or ethanol or any other organic solvent less than the amount required to enable solubility of the enteric material under the processing conditions. Preferably, the amount of added organic solvent is less than about 0.1 percent by weight of the combination of water, emulsifier and enteric material.

In one embodiment, the water is deionized water.

The enteric matrix material used herein is any food grade enteric polymer, of a combination or two or more food grade enteric polymers. Preferably, the enteric matrix material is either shellac or zein or a combination thereof. As discussed below, the ratio of shellac to zein can be predetermined to achieve the desired release rate after ingestion, with a decreased release rate corresponding with an increased ratio of shellac to zein. The shellac can commercially be provided as an alakaline (pH>7) aqueous solution, such as a water-based solution having a solid content of about 25 percent by weight or it can be prepared from commercially available refined, bleached and dewaxed shellac powder. The shellac dilution is substantially free of organic solvent, although it may contain trace amounts of organic solvents, such as isopropyl alcohol (such as can be included in commercial products), to act as a carrier for other ingredients in the shellac solution, such as methyl and propyl parabens. Preferably, the prepared shellac solution does not contain any organic solvents.

Preferably, the enteric matrix material comprises a combination of shellac and zein, with zein comprising at least about 5.0 percent of the enteric matrix material by dry weight. Due to differences in hydration and solubility of zein and shellac, particularly the solubility at varying pHs and rates of hydration and solubility, different ratios of shellac to zein provide different enteric dissolution properties as well as differing degrees of core material protection in the final product, such as beverages.

The emulsifier described herein is any food grade emulsifier. In preferred embodiments, the emulsifier is polysorbate, polyglycerol ester, sucrose stearate, sucrose esters, proteins, lecithins or combinations thereof.

Generally, water comprises about 50.0 percent to about 95.0 percent of the dispersion by weight and preferably from about 70.0 to about 95.0 percent, and more preferably from about 80.0 to about 90.0 percent. The emulsifier generally comprises less than about 5.0 percent of the dispersion by weight, preferably from about 0.01 to about 1.0 percent by weight, and more preferably about 0.01 to about 0.1 percent by weight of the dispersion. The zein, shellac or combinations thereof ranges from about 1.0 percent to about 10.0 percent by weight, preferably from about 4.0 to about 9.0 percent, and more preferably from about 5.0 percent to about 8.0 percent by weight of the dispersion.

Upon forming the dispersion, a hydrophobic liquid is added 200 and agitated to provide a coarse emulsion having a droplet size of more than about 10 micrometers. After the coarse emulsion is formed, the coarse emulsion is subjected to homogenization to create a fine, stable emulsion 300. The fine, stable emulsion has a droplet size of less than about 10 micrometers. Within the fine emulsion, the hydrophobic liquid is homogeneously dispersed in the form of fine droplets throughout. Preferably, the hydrophobic liquid is added in amount ranging from about 2.0 to about 7.0 percent of the emulsion by weight. More preferably, the hydrophobic liquid is added in an amount ranging from about 3.0 to about 6.0 percent of the emulsion by weight. The emulsion includes from about 60.0 to about 95.0 percent water.

As used herein, "homogenization" or "homogenized" refers to the use of a rotor/stator mixing device operating at a speed greater than 10,000 RPM or a valve homogenizer operating at a pressure of 500-10,000 psi.

The hydrophobic liquid can comprise any mixture of hydrophobic liquids and solids, such as solids mixed or combined therewith or dissolved or solubilized therein. As an example, hydrophobic liquid can be selected to include materials which are desired to be released in the small intestine rather than the stomach due to pH sensitivity. As an example, the hydrophobic liquid can include compositions described in U.S. Patent Publication No. 2008/0145462 to Enan. For example, the hydrophobic liquid includes 25-35% by weight para-cymene, 1-10% by weight linalool, 1-10% by weight alpha-pinene, 35-45% by weight thymol, and 20-30% by weight soybean oil.

In particular, the hydrophobic liquid described herein can include an essential oil blend which possesses anti-parasitic properties. In one preferred embodiment, organic compounds are blended with food grade oil, i.e. soybean oil. Further, the organic compounds can include thymol and linalool. In a further preferred embodiment, the organic compounds further include alpha-pinene and para-cymene. As discussed in the examples below, one exemplary blend includes, by weight, about 17.5 percent soybean oil, about 8 percent alpha-pinene (liquid), about 44 percent para-cymene (liquid), about 5 percent linalool (liquid) and about 25.5 percent Thymol (crystal). In an alternative embodiment, the hydrophobic liquid includes esters, such as esters of linalool and thymol, as described in co-pending application Ser. No. 12/479,444, filed the same day as this application and which is incorporated herein by reference.

Other suitable examples of a hydrophobic liquid include unsaturated and polyunsaturated OMEGA 3, other unsaturated and polyunsatured lipids or fatty acids and triglycerides thereof, beta-carotene, and oil soluble vitamins, stomach irritants, or any other hydrophobic materials that are either sensitive to acidic pH conditions or impart strong undesirable taste.

The emulsion is then acid titrated 400. During acid titration the emulsion can be subjected to agitation or homogenization (not high pressure homogenization), preferably agitation. Acid is titrated in an amount effective to decrease the pH below the isoelectric point, such as a pH of about 7.0, causing phase separation and inducing precipitation of the enteric matrix out of solution with the hydrophobic liquid being microencapsulated therein, thus creating a slurry of an aqueous solution and precipitate. The slurry includes a particulate precipitate having a particle size from about 1.0 to about 1000.0 micrometers, preferably about 10.0 to about 500.0 micrometers, and more preferably from about 75.0 to about 250.0 micrometers. More preferably, precipitation occurs at a pH ranging from about 3.0 to about 6.5, and preferably from about 3.0 to about 5.0.

While not wishing to be limited by theory, it is believed that as the pH of the emulsion drops below the isoelectric point, both the shellac and zein particles may cross-link to like particles or to one another to form a matrix, the hydrophobic liquid being microencapsulated within the matrix. As a result of the cross-linking, the hydrophobic liquid is homogeneously dispersed throughout the matrix. The matrix further provides a seal for the hydrophobic liquid. As a result, the impact of the hydrophobic liquid on the organoleptic qualities of the finished powder is correlated to any hydrophobic liquid remaining adhered to the outer surface of the enteric matrix.

The acid can be any food grade acid. More preferably, the acid is a weak food grade acid. Further, in a preferred embodiment the acid is citric acid.

As noted above, the composition of the enteric matrix material affects the dissolution rate and the protection provided by the enteric matrix. As a result, the rate and amount of acid addition varies based on the enteric matrix materials used.

To reclaim the precipitate, the slurry is filtered 500, washed 600 and dried 700. In one embodiment, the slurry is filtered, the resultant slurry cake is then washed and refiltered prior to drying. Preferably, the surface oil on the outer surface of the particulate precipitate is less than about 1.0 percent by weight of the final product.

In a preferable embodiment, a surface oil remover is added after filtering to aid in removing residual surface oil from the precipitate, as described in co-pending application Ser. No. 12/479,433, filed the same day as this application and which is incorporated herein by reference. Further, the surface oil remover can also be added prior to the refiltering step.

After the precipitate has been filtered and washed, the precipitate is dried to form a powder. Drying can be conducted at room temperature such that the powder has a moisture content of less than about 10.0 percent, more preferably to a moisture content of about 5.0 to about 6.0 percent.

Further, the powder can be pulverized using known methods to reduce the particle size of the powder precipitate, and then further dried to a moisture content of less than about 5.0 percent by known methods, such as with a fluidized bed dryer. The resultant particles have a particle size ranging from about 1.0 to about 1000.0 micrometers, preferably from about 10.0 to about 500.0 micrometers, and more preferably from about 75.0 to about 250.0 micrometers.

When drying the powder, the temperature should be maintained between about 25 C to about 70 C, preferably 35 C to about 60 C, and more preferably between 35 C and 45 C. During other processing steps, it is preferable to maintain the temperature between about 4 C to about 40 C, more preferably 4 C to 30 C, and further preferable from about 15 C to about 28 C.

The resultant powder can be further processed, such as applying a coating of enteric material around the enteric matrix. The enteric coating material can include any food grade enteric polymer.

EXAMPLE #1

100 Percent Shellac as the Enteric Matrix Material

An essential oil blend was prepared by blending 8 percent alpha-pinene (liquid), 44 percent para-cymene (liquid), 5 percent linalool (liquid), 25.5 percent Thymol (crystal), and 17.5 percent soybean oil. Mixing in a glass beaker with stirring bar was typically carried out until all of the Thymol crystals are dissolved.

In a large beaker the following steps were carried out in the order specified: 1200 g of deionized (DI) water was added to the beaker, and then 300 g of the stock solution of 25 percent shellac (MarCoat solution from Emerson Resources Inc.) was mixed in under agitated conditions such that the pH of solution ranges from about 7.2 to about 9.0. While agitating, 0.8 g of polysorbate 85 was added and mixed for 1-2 minutes for full dispersion. Next, 35 g of essential oil blend was slowly added under agitated conditions to form a coarse emulsion. Once the whole amount of oil was dispersed, the mix was homogenized at 12500 rpm for 5 minutes using Fisher Scientific PowerGen 700D Homogenizing System with 200 mm×25 mm Generator.

The emulsion was then subjected to agitation and, while mixing, 2.0 percent citric acid solution was titrated in at slow rate while monitoring the resultant change in pH. Titration continued until the pH reached 4.4, after which $SiO_2$ (AB-D from Pittsburgh Plate Glass Industries) was added (5 g $SiO_2$, in 200 g water, and the slurry was mixed for 15-20 minutes.

The slurry was then filtered by pouring the slurry over a 200 mesh screen with 75 micrometer holes. The particulates on the top of the screen were resuspended in 1000 g water with 3.5 g $SiO_2$. The slurry was mixed for 30-60 seconds and then re-filtered. The washing was repeated one more time as above, the filtrate was collected, spread on tray and allowed to dry at room temperature for overnight (to a moisture content of between about 5.0 to about 6.0 percent).

A sample was analyzed for percent Payload of each component and total.
Results: Total payload=17.5 percent
Alpha-pinene=0.7 percent
Para-cymene=3.2 percent
Linalool=1.0 percent
Thymol=7.0 percent
Soybean oil=5.6 percent

EXAMPLE 2

Scalability of the Process Using 100 Percent Shellac as a Matrix Material 12 kg of water was added to a mixing tank, then 3 kg of 25 percent shellac solution was added and mixed with the water, the whole mixture was adjusted to a pH of about 8.0 by adding 10.0 percent sodium hydroxide solution. 5 g of sucrose stearate was added and mixed for 1-2 minutes, and then 400 g of essential oil blend (as described in Example 1) was added slowly. The mixture was homogenized as in Example 1 to prepare a stable emulsion.

The emulsion was then titrated with 2 percent citric acid solution until pH reached 4.4, and then 75 g of $SiO_2$ was added and mixed in for about 20 minutes. The slurry was then filtered using a 200 mesh (75 micrometer) screen. The filter cake was re-suspended in 20 lb of water with 50 g $SiO_2$, mixed for about 5 minutes, and then re-filtered on a 200 mesh screen. The washing was repeated one more time, and the final filter cake was spread on a large tray for overnight drying at room temperature. The next day, the product was pulverized in a warring blender, and then fluid bed dried at 40 C. Collected powder was sifted through a 35 mesh (500 micrometer) screen. (See FIG. 2 for the compositional analysis).

EXAMPLE #3

100 Percent Zein Powder (Corn Proteins) as the Enteric Matrix Material 75 g of zein (F4000 from Freeman Industries) powder and 1200 g of DI water was combined in a large beaker, the zein then dispersed in the water with agitation. Once the zein powder was completely dispersed, 10 percent sodium hydroxide solution was slowly titrated until the pH reached 11.3. At this pH, the zein powder was completely solubilized. Next, 0.7 g of polysorbate 85 was added, agitated for 1-2 minutes, and then 30 g of essential oil blend (as in Example 1) was added. The mixture was homogenized as in Example 1. The emulsion was then titrated with 2 percent citric acid solution (as in Example 1) until pH reached 4.6. The slurry was mixed for 15-20 minutes.

Filtering and washing was conducted as in example #1, except no $SiO_2$ added. Filtrate was collected and dried on a tray at room temperature for overnight. Sample was analyzed for percent payload of each component and total.
Results: Total payload=19 percent
Alpha-pinene=0.9 percent
Para-cymene=4.1 percent
Linalool=0.9 percent
Thymol=6.5 percent
Soybean oil=6.7 percent

EXAMPLE #4

Scalability of the Process Using 100 Percent Zein as the Enteric Matrix Material In a large mixing tank with propeller overhead mixer, 12 kg of water was added in to the tank, and then 10 g of sucrose ester (S-1570 from Mitsubishi Kagaku Corporation, Tokyo, Japan) was dispersed in the tank. 750 g of zein powder was dispersed in, and then 10 percent sodium hydroxide solution was metered in while mixing until pH reached 11.3. The dispersion was mixed until the zein powder was completely dissolved. Next, 400 g of essential oil blend (as in Example 1) was slowly added. Once all the oil was dispersed, the mixture was homogenized for 5 minutes to create an emulsion as in Example 1.

The emulsion was then titrated with 2 percent citric acid solution under agitation until pH reached 3.8. The slurry was allowed to mix for an extra 10 minutes. The mixture was transferred into separate containers, allowed to stand for a few minutes so the precipitated particulates could settle at the bottom.

The supernatant was decanted onto a large 200 mesh screen followed by screening the remaining particulates. The filtrate on top of the screen was re-suspended in 9 kg of acidified water (pH 3.5), containing 20 g $SiO_2$, mixed for a few minutes and then decanted and filtered. This washing step was repeated one more time, the rinse water containing 20 g $SiO_2$, after filtering the filter cake was collected, spread thin on a tray and allowed to dry overnight at room temperature. The semi-dry powder was pulverized and then fluid bed dried at 40° C. to target moisture (less than 5 percent). Final product was sifted through a 35 mesh (500 micrometer) screen. See compositional analysis in FIG. 2.

EXAMPLE 5

Matrix Containing 75 Percent Shellac & 25 Percent Zein

Similar to example 4, 12 kg of water was added to a mixing tank, 7.5 g of sucrose stearate (S-1570) was added and mixed for 1-2 minutes. Then 2.25 kg of 25 percent shellac solution was added, followed by 187.5 g zein powder. 10 percent sodium hydroxide was metered in until pH reached 11.3 (to solubilize zein). Once the zein powder was completely in solution, 400 g of essential oil blend (as described in Example 1) was added. The mixture was homogenized as in Example 1, and then the emulsion was titrated to pH 3.9 with citric acid solution. 75 g of SiO2 (Flow Guard AB-D) was added and mixed for about 20-30 minutes. Filtering, washing, and drying processes were carried out in a similar fashion as described in example 4. Final powder was sifted through 35 mesh (500 micrometer) screen. See FIG. 2 for compositional analysis.

EXAMPLE #6

In Vitro Testing of Simulated Release in Stomach and Small Intestine

This example is intended to show the release rate and profile of actives from the matrix of the microcapsules from Examples 2, 4, and 5. Release from enteric microcapsule samples was evaluated by sequential simulation in Stomach Simulation Solution (10 mg/ml pepsin, 2 mg/ml NaCl, pH 2.0) for 30 min followed by Small Intestinal Simulation Solution (10 mg/ml pancreatin, 2.4 mg/ml bile salt, pH 6.8) for up to 24 hr at 37 C. Samples were taken at pre-determined time intervals and analyzed for release of individual actives.

Figures 2, 3:
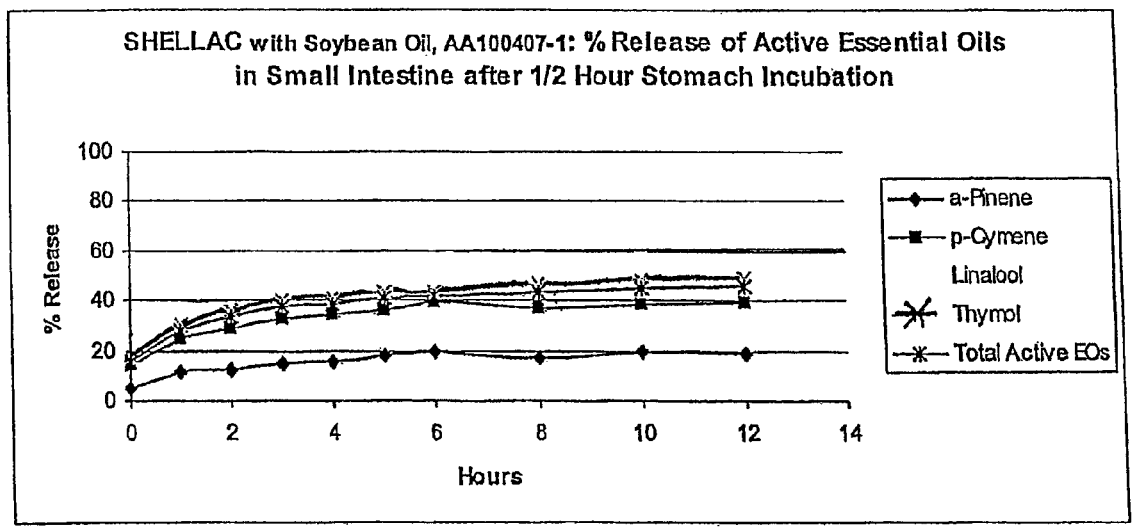
FIG. 2 is an analysis of the products of Examples 2, 4 and 5.
FIGS. 3-5 illustrate release rates of the hydrophobic liquid using various enteric matrix materials as discussed in Example 6.
Figure 4:
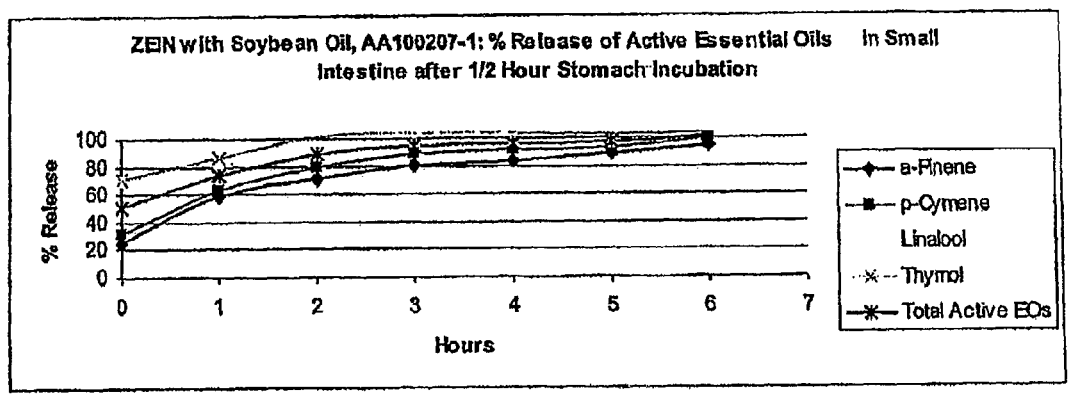
Figure 5:
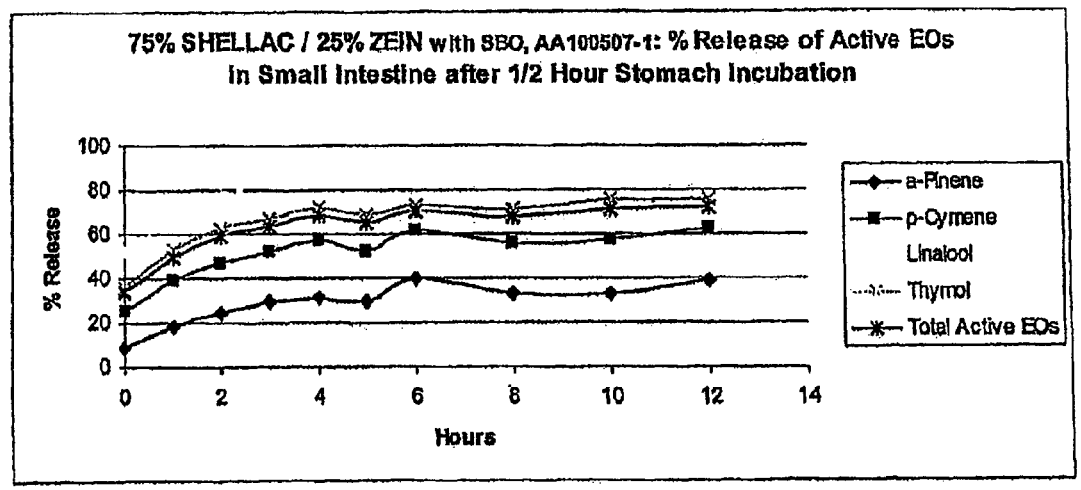

The release profile is different for the three compositions. When the matrix was made up of 100 percent shellac (as seen in FIG. 3), the release continued to have a gradual increase but never reached complete release even after 12 hrs. On the other hand, the release can be characterized as having a quicker release rate and higher total release when the matrix is made up of 100 percent zein (about 80 percent of the total pay load is released at the first hour in the intestinal conditions) (see FIG. 4). The combination of the shellac and zein (See FIG. 5) show a higher rate than 100 percent shellac, but lower than 100 percent zein, and the release seem to be sustained at a slow rate with a maximum after 6 hours.

EXAMPLE #7

This Example Demonstrates the Microencapsulation of Oil Blend Containing Two Esterified Components (Thymol Acetate and Linalool Acetate in Combination with Alpha-pinene, Para-cymene, and Canola Oil)

In a beaker, 2400 g of water was added and then, with agitated mixing, 7.5 g of zein powder was dispersed in the water. 10 percent sodium hydroxide solution was metered into the dispersion until pH reached 11.3 (to solubilize the zein powder). Next, 570 g of 25 percent shellac solution and 1.0 g sucrose stearate (S-1570) were added, followed by 70 g essential oil blend (18.8 percent canola oil, 8.6 percent alpha-pinene, 39.8 percent para-cymene, 5.4 percent Linalool acetate, 27.4 percent Thymol acetate), which was added slowly to the mix. The emulsion was then homogenized (as in Example 1) using a Fisher Scientific PowerGen 700D Homogenizing System with 200 mm×25 mm Generator at 15000 rpm for 4 minutes, then at 20000 rpm for 1 minute.

The emulsion was then titrated with 3.0 percent citric acid solution to pH 4. Then, 280 g of 10 percent sodium chloride solution was added in, and 15 g SiO2 was added and allowed to mix for 30 minutes. The slurry was then filtered and washed similar to that described in example #1. The washed filter cake was spread on a tray to dry overnight, and then further dried in a fluid bed dryer at 40 C, powder was sifted and product passing through 35 mesh (500 micrometers) size was collected. Final moisture was 4.7 percent.

Figure 6:
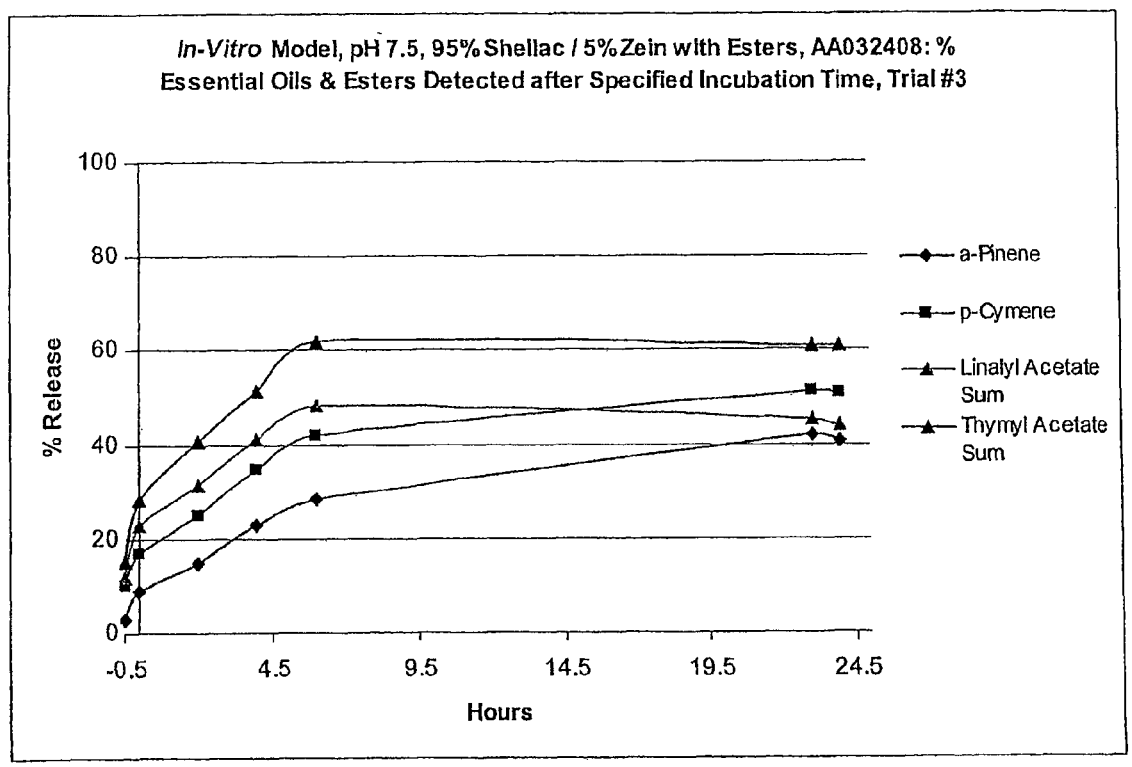
FIG. 6 illustrates the release rate of the hydrophobic liquid including esters therein as discussed in Example 7.

The release rate is shown in FIG. 6. In particular, while the overall release of the essential oil composition was not as high as in FIGS. 3-5, the initial release (through 1 hour) was lower than the compositions illustrated in FIGS. 3-5.

Analysis:
Total payload=18.3 percent
Alpha-pinene=0.9 percent
Para-cymene=3.8 percent
Linalool acetate=1.2 percent
Thymol acetate=6.6 percent
Canola oil=5.8 percent

EXAMPLE #8

Preparing Cream Wafer with Microencapsulated Essential Oil Wafer Filling

White cream filling was prepared by mixing in a Hobart mixer, pre-melted 750 g of San-Trans fat plus 0.5 g of liquid soy lecithin, with confectionary sugar (powder sugar), until smooth and homogeneous. Filling was transferred into a container and cooled down for later use.

Wafer cracker sheets were purchased from local grocery store. 97.8 g of cream filling was softened by warming up in a microwave oven. To filling, the following was added: 1.46 g of microencapsulated material, 0.15 g citric acid, 0.5 g Lemon oil flavor, one drop of beta-carotene for yellow color. The filling was spread on the cracker sheet (1-2 mm thick), and then another sheet was applied onto the top. The cracker sheet sandwich was then cooled in a refrigerator for about 30 minutes, and then it was cut to different sizes (cracker size). A similar formulation, double and triple layer crackers were also prepared. Other flavor varieties were also evaluated including chocolate and fruit flavors.

EXAMPLE 9

Cracker Sandwich with Filling Including the Microencapsulated Material

A cracker sandwich with microencapsulated powder incorporated into the filling was prepared as follows:
Filling:
1) Fat portion: In a glass beaker, 2000 g of Shortening San-Trans 39 was melted in microwave oven for about 3 minutes until it became a clear liquid, 0.8 g of soy lecithin was added.

2) Solid blend portion: In a Hobart mixer, the following was dry blended: 100 g lactose, 10 g salt, and 249.4 g Maltodextrin (5 D.E.).

The melted fat was poured onto the dry blend in the Hobart Mixer, and allowed to mix for at least 5 minutes (to form a homogeneous mix). The filling was transferred into a container and used as a stock filling. Cracker sandwich: 100 g of cheese filling was warmed up in a microwave oven for 30 seconds and to the softened filling, 1.4 g of the microencapsulated material was mixed in, and also various seasoning and flavor blends. 18 g of the filling was sandwiched between two crackers, and allowed to cool down. Different flavor varieties of cracker sandwiches were evaluated including, nacho, taco, Italian herb, and oriental seasoning. Filling was also evaluated with different type of crackers, including Saltine, Ritz and others. When evaluated, the crackers containing microencapsulated essential oil were pleasantly acceptable.

EXAMPLE 10

This Example Demonstrates the Encapsulation of the Essential Oils, Followed by Surface Oil Removal as Disclosed in co-pending application Ser. No. 12/479,433.

In a beaker, 2400 g of water was added in and then with overhead low shear mixing, 37.5 g of zein powder was dispersed in. 10% sodium hydroxide solution was metered in until pH reached 11.3 (to solubilize the zein powder). 450 g of 25% shellac solution was added in. 1.4 g sucrose stearate (S-1570) was added in, and then 80 g essential oil blend (13% canola oil, 10% alpha-pinene, 25% Para-cymene, 12% Linalyl acetate, 40% Thymol acetate) was added slowly to the mix. The emulsion was then homogenized using an IKA Works T25 Basic Ultra Turrex with 200 mm×20 mm Generator at 17,500 rpm for 1 minute, then at 24,000 rpm for 5 minutes.

The emulsion was then titrated with 3% citric acid solution until the pH reached 3.8. Then, 15 g SiO2 (Flo Guard FF, average size of 18 micrometers) was added in and allowed to mix for 30 minutes. The slurry was then filtered by pouring over a filter cloth with <5 micro-meters holes. The particulates on the filter cloth were then resuspended into 2000 g water containing 0.5 g citric acid, 0.5 g sucrose stearate (S-1570), and 7.5 g SiO2 (Flo Guard FF). The slurry was mixed for 15 minutes and then re-filtered. The washing was repeated one more time as above, then filter cake was collected. The filter cake was then pressed by placing in a 30 micrometers filter bag in a press box and squeezing in a cheese press at 20 psi for 20 minutes to remove more of the water. The press cake moisture was 18.8%.

The press cake was mixed with 50 g SiO2 (Flo Guard FF) in a 5 quart Hobart mixer with a whip at speed set at 1 for 5 minutes. The material from the Hobart mixer was ground in a Fitz Mill Model DA S06 Comminutor with hammers forward at the highest speed using a 1532-0020 perforated plate. The ground material was tumbled using jar tumblers for 60 minutes. The batch was then dried in a Uni-Glatt Fluid Bed Dryer at 40° C. for 20 minutes. The dried batch was screened and only particles between 75-250 micrometers were collected.

|  | % alpha-Piene | % para-Cymene | Linalyl acetate | Thymyl acetate | Total |
| --- | --- | --- | --- | --- | --- |
| Total Loading | 0.84 | 2.70 | 1.50 | 6.40 | 11.44 |
| Surface Oils | <0.001 | 0.007 | 0.003 | 0.021 | 0.031 |

EXAMPLE #11

Preparing a Powdered Beverage with Microencapsulated Material

Fruit flavored powdered beverages were purchased from a supermarket, and both orange and mango type were used to prepare a low pH powdered soft drink. Powdered soft drinks such as fruit based type are ideal for the delivery of enteric active compounds for several reasons: 1) The powdered drink can easily be dry blended with microencapsulated material, and provide shelf stability for extended period of time, 2) when reconstituted, the beverage has an acidic pH (similar to stomach pH), no early release, and, therefore, no adverse effect on taste, 3) Beverages are typically consumed within a very short period of time.

The orange type powdered beverage was sweetened with sugar and artificial sweetener and was dry blended with the microencapsulated essential oil from example #10. A single serve portion, such as about 7 g of orange powder, was dry blended with 0.48 g of microencapsulated powder (active payload=11.44 percent), the amount selected to provide the desired functional benefit of the microencapsulated hydrophobic liquid. Additionally 0.35 g of Carboxy methyl celluolose (CMC 7HXF) was added to the dry blend to provide extra viscosity and better suspendability. The dry blend was reconstituted into 200 ml of cold water. The beverage was tasted after 5 & 60 minutes after reconstitution by an informal sensory panel. Testing by a sensory panel demonstrated successful masking of the essential oil blend in the orange type beverage.

A similar evaluation was made with mango type beverage with similar results.

While the invention has been particularly described with specific reference to particular process and product embodiments, it will be appreciated that various alterations, modifications, and adaptations may be based on the present disclosure, and are intended to be within the spirit and scope of the invention as defined by the following claims.

What is claimed is:

1. A method of microencapsulating an active ingredient with an enteric matrix, the method comprising:
    a) agitating a combination of water, an enteric matrix material, and an emulsifier at a pH above a solubility of the enteric matrix material to maintain complete dissolution of the enteric matrix material, the combination substantially free of organic solvents, wherein the enteric matrix material is selected from the group consisting of non-deamidated zein, shellac, and mixtures thereof;
    b) adding a hydrophobic liquid to the combination;
    c) homogenizing the hydrophobic liquid and the combination to create an emulsion; and
    d) acid titrating the emulsion under agitated conditions in an amount effective to form a particulate precipitate having enteric functionality, wherein the acid is a food grade acid, and wherein the emulsion is free of oppositely charged particles.

2. The method of claim 1 wherein the emulsion is acid titrated to a pH in the range of about 3.0 to about 6.5.

3. The method of claim 1 further comprising (e) filtering, washing and drying the particulate precipitate to produce a dry powder.

4. The method of claim 1 further comprising (b1) agitating the hydrophobic liquid and combination to create a coarse emulsion prior to homogenization.

5. The method of claim 1 further comprising (d1) adding a surface oil remover to the particulate precipitate in an amount effective to reduce residual surface oil.

6. The method of claim 1 further comprising (a1) adding a base in an amount effective to adjust the pH to about 7.1 to about 12.0.

7. The method of claim 6 wherein the base is sodium hydroxide.

8. The method of claim 6 wherein the base is potassium hydroxide.

9. The method of claim 6 wherein the base is ammonium hydroxide.

10. The method of claim 1, wherein the enteric matrix material is selected for providing a specific release rate.

11. The method of claim 1 wherein the emulsifier is a food grade emulsifier.

12. The method of claim 1 wherein the emulsifier is selected from the group consisting of polysorbate, polyglycerol ester, sucrose stearate, sucrose esters, protein, lecithin and mixtures thereof.

13. The method of claim 1 wherein the hydrophobic liquid comprises an essential oil.

14. The method of claim 1 wherein the hydrophobic liquid comprises linalool and thymol.

15. The method of claim 1 wherein the hydrophobic liquid comprises alpha-pinene, para-cymene, linalool and thymol.

16. The method of claim 15 wherein the hydrophobic liquid includes a triglyceride.

17. The method of claim 1 wherein the hydrophobic liquid comprises linalyl ester and thymyl ester.

18. The method of claim 1 wherein the hydrophobic liquid comprises unsaturated and polyunsaturated fatty acids.

19. The method of claim 1 wherein the hydrophobic liquid comprises unsaturated and polyunsaturated lipids.

20. The method of claim 1 wherein the hydrophobic liquid comprises beta-carotene.

21. The method of claim 1 wherein the hydrophobic liquid comprises oil soluble vitamins.

22. The method of claim 1 wherein the hydrophobic liquid comprises a triglyceride.

23. The method of claim 22 wherein the triglyceride is soybean oil.

24. The method of claim 21 wherein the triglyceride is canola oil.

25. The method of claim 1 wherein the acid is citric acid.

26. The method of claim 1 wherein the combination includes from about 0.01 to about 5.0 percent by weight emulsifier.

27. The method of claim 1 wherein the emulsion comprises from about 2.0 to about 7.0 percent by weight hydrophobic liquid.

28. The method of claim 1, wherein the particle precipitate has a particle size ranging from about 1.0 to 1000.0 microns.

29. A method of microencapsulating an active ingredient with an enteric matrix, the method comprising:
  a) agitating a combination of water, an enteric matrix material, and an emulsifier at a pH above a solubility of the enteric matrix material to maintain complete dissolution of the enteric matrix material, the combination substantially free of organic solvents, wherein the enteric matrix material is selected from the group consisting of non-deamidated zein, shellac, and mixtures thereof;
  b) adding a hydrophobic liquid to the combination;
  c) homogenizing the hydrophobic liquid and the combination to create an emulsion; and
  d) acid titrating the emulsion to a pH at or below an isoelectric point of the enteric matrix material under agitated conditions with a food grade acid in an amount and for a time effective to form a particulate precipitate having enteric functionality, without substantial degradation of the enteric functionality, and wherein the emulsion is free of oppositely charged particles.

30. The method of claim 1, wherein the particulate precipitate includes the hydrophobic liquid homogeneously dispersed throughout a matrix of the enteric matrix material.

31. The method of claim 29, wherein the particulate precipitate includes the hydrophobic liquid homogeneously dispersed throughout a matrix of the enteric matrix material.

* * * * *